US009877787B2

(12) United States Patent
Brabrand et al.

(10) Patent No.: US 9,877,787 B2
(45) Date of Patent: Jan. 30, 2018

(54) NEEDLE HOLDER

(71) Applicant: NeoRad AS, Oslo (NO)

(72) Inventors: Knut Brabrand, Oslo (NO); Nicolay Berard-Andersen, Oso (NO); Gjermund Fjeld Olsen, Oslo (NO); Vegard Bakke, Oslo (NO)

(73) Assignee: NEORAD AS, Oslo (NO)

( * ) Notice: Subject to any disclaimer, the term of this patent is extended or adjusted under 35 U.S.C. 154(b) by 812 days.

(21) Appl. No.: 14/305,037

(22) Filed: Jun. 16, 2014

(65) Prior Publication Data

US 2014/0336670 A1    Nov. 13, 2014

Related U.S. Application Data

(63) Continuation of application No. 13/144,107, filed as application No. PCT/GB2010/000101 on Jan. 21, 2010, now abandoned.

(30) Foreign Application Priority Data

Jan. 22, 2009   (GB) .................................. 0901072.9

(51) Int. Cl.
*A61B 90/11* (2016.01)
*A61B 19/00* (2006.01)
*A61B 17/34* (2006.01)
*A61B 17/00* (2006.01)

(52) U.S. Cl.
CPC ............ *A61B 19/201* (2013.01); *A61B 90/11* (2016.02); *A61B 2017/00477* (2013.01); *A61B 2017/3407* (2013.01)

(58) Field of Classification Search
CPC ........ A61B 890/11; A61B 2017/00477; A61B 2017/3407; A61B 90/11
See application file for complete search history.

(56) References Cited

U.S. PATENT DOCUMENTS

| | | | |
|---|---|---|---|
| 4,883,053 A | 11/1989 | Simon | |
| 5,201,742 A | 4/1993 | Hasson | |
| 6,361,499 B1 | 3/2002 | Bates et al. | |
| 7,332,990 B2 | 1/2008 | Mark et al. | |
| 2002/0032380 A1* | 3/2002 | Acker .................... | A61B 34/20 600/439 |
| 2004/0064148 A1 | 4/2004 | Daum et al. | |
| 2005/0049486 A1* | 3/2005 | Urquhart ................ | A61B 90/14 600/429 |
| 2005/0113816 A1 | 5/2005 | Whitmore, III et al. | |
| 2005/0131291 A1 | 6/2005 | Floyd et al. | |
| 2005/0143753 A1 | 6/2005 | Whitmore, III et al. | |

FOREIGN PATENT DOCUMENTS

| | | |
|---|---|---|
| EP | 1 929 972 A1 | 6/2008 |
| WO | 2006/081409 A2 | 8/2006 |
| WO | 2008062474 A2 | 5/2008 |

* cited by examiner

*Primary Examiner* — Peter Luong
(74) *Attorney, Agent, or Firm* — Eversheds Sutherland (US) LLP

(57) ABSTRACT

A needle holder for use in an image guided intervention procedure. The needle holder includes a clip for holding a needle and a guide arrangement for supporting the clip and directing the needle at a desired angle relative to a patient's body. The clip includes a releasable connection such that the needle can be disengaged from the guide arrangement by a lateral movement of the clip and/or the guide arrangement relative to the longitudinal axis of the needle.

22 Claims, 11 Drawing Sheets

NEEDLE HOLDER

RELATED APPLICATIONS

The present application is a continuation of U.S. Ser. No. 13/144,107, filed on Sep. 28, 2011. U.S. Ser. No. 13/144,107 is incorporated herein by reference in full. The present application likewise claims priority to International Application No. PCT/GB2010/000101, filed on Jan. 21, 2010; U.S. Provisional Ser. No. 61/206,326, filed on Jan. 28, 2009; and GB 0901072.9, filed on Jan. 22, 2009. These applications are incorporated herein by reference in full.

TECHNICAL FIELD

The invention relates to a needle holder for use in image guided interventions.

BACKGROUND OF THE INVENTION

Interventional radiology is a subspecialty of radiology in which minimally invasive procedures are performed using image guidance. Some of these procedures are done for purely diagnostic purposes (e.g., biopsy), while others are done for treatment purposes (e.g., radio frequency ablation). Pictures (images) are used to direct these procedures, which are usually done with needles or small catheters that are inserted into the body through the skin or through a body cavity or anatomical opening. The images allow the interventional radiologist to guide these instruments through the body to the areas of interest.

Common interventional imaging methods include X-ray fluoroscopy, computed tomography (CT), ultrasound (US), and magnetic resonance imaging (MRI).

When starting an interventional procedure the needle is introduced a little into the patient from a selected entry point. To verify the correct position and direction a set of control images are taken. Due to the weight of the needle, especially the weight of the portion of the needle which is outside the body, gravity will deflect the needle from its intended path. This makes it difficult to ensure that the needle hits the intended target, which can be a small area in the body.

The conventional approach is to advance towards the target by repeatedly adjusting the angle and inserting the needle little by little while constantly taking repeat images to verify position and direction. Every time an image is acquired any deflection of the needle would make an assessment of the correct direction more difficult. As the depth of the needle increases more tissue is there to support the needle. However, a heavy needle and/or a long needle would still suffer a deflection due to gravity and superficial lesions would not have enough tissue to stabilize a needle.

It is known to use a needle holder to guide and stabilize the needle at a chosen angle during image acquisition. When using a needle holder the user will get a firm idea of the planned direction of the needle and can use this information to redirect the needle until the correct angle is obtained. Once the desired angle is obtained the needle holder can help to steer the needle in the chosen direction, and when the needle is at the correct position the needle holder can be used to fix the needle at a chosen depth (when using a coaxial approach). Longer needles and/or heavier needles would typically need more support than short and light weighted ones.

Examples of known needle holders can be found in U.S. Pat. No. 4,883,053, U.S. Pat. No. 5,201,742 and WO 2004/021898. These documents disclose the use of a plate or base which is placed onto the patient and supports two guide members that intersect at an angle. The guide members are typically semi-circular or segments of a circle which are connected at their ends over two diameters of a circular base, where the diameters intersect at right angles. One or both of the guide members is connected to the base with hinges that enable rotation of the guide member to different angles. A clip or a tube for holding the needle is joined to the guide members in such a way that the needle can be pointed at any angle relative to the plane of the base. This is achieved by allowing the clip or tube to slide relative to one or both of the guide members, and by changing the angle of the guide members. A screw fitting can be used to tighten the connection between the clip or tube and the guide members, and/or between two guide members in order to fix the needle in place.

It is also known in alternative embodiments in some of the above references to use a spherical or part-spherical member which is moveably mounted to a part-spherical bearing surface to enable a needle passing through the spherical or part-spherical member to be pointed at a desired angle.

However, whilst these prior art devices can provide the necessary stability and guidance for a needle in an interventional radiology procedure, they restrict the actions of the radiologist in subsequent or preceding handling of the needle.

SUMMARY OF THE INVENTION

Viewed from a first aspect, the present invention provides a needle holder for use in an image guided intervention procedure comprising: a clip for holding a needle and a guide arrangement for supporting the clip and directing the needle at a desired angle relative to the patient's body; wherein the clip includes a releasable connection such that the needle can be disengaged from the guide arrangement by a lateral movement of the clip and/or the guide arrangement relative to the longitudinal axis of the needle.

In the prior art, the needle is secured to the guide members in such a way that the needle can only move relative to the guide member along the longitudinal axis of the needle. Thus, in order to remove the needle from the guide arrangement the whole length of the needle must pass through the needle holder. The inventors have realised that this creates significant problems for the user, as it means that the user cannot abort the use of the needle holder without retracting the needle from the patient. The prior art needle holders must remain in place whilst the needle is in use during an interventional procedure. The clip of the present invention allows the needle to be released from the guide arrangement by a lateral movement, and thus enables the needle holder to be disconnected from the needle at any stage, and at any point along the length of the needle. The needle holder of the invention can advantageously be removed from the needle and from the patient without moving the needle relative to the patient's body. The user can decide part-way through a procedure if a needle holder is or is not necessary, and can connect or disconnect the needle holder accordingly. The needle may remain in place during disengagement of the clip, because the lateral movement permits removal of the clip without the need for movement of the needle relative to the body. In addition, once the needle has been inserted sufficiently for the body tissue to provide appropriate support and guidance, the needle holder of the present invention can be disconnected to enable full insertion of the whole length of the needle if required.

The needle holder preferably comprises a base for supporting the needle holder on the patient's body. Advantageously, the lateral movement of the clip and/or the guide arrangement is a movement of the clip and/or the guide arrangement without requiring movement of the needle relative to a base of the needle holder. Although in some instances it may be beneficial to move the base away from the patient's body as the needle is disconnected, it will often be desirable to disconnect the needle without movement of the needle relative to the body. By using an arrangement that does not require movement of the base relative to the needle, both the base and the needle can remain in situ as the clip is released. Once disconnected from the needle, the needle holder can be easily removed.

Advantageously, the clip holds the needle by releasably securing the needle to the needle holder.

The releasable connection may comprise a connection between the clip and the guide arrangement and/or a connection between the clip and the needle. In a preferred embodiment, the releasable connection enables the needle to be disconnected from the clip by a lateral movement of the clip relative to the longitudinal axis of the needle. This arrangement means that the needle can be released from the guide member and also from the clip.

Preferably, the clip includes a first connector for releasable engagement with the guide arrangement, and a second connector for releasable engagement with the needle. With this arrangement, the clip can be fully disconnected from both the guide arrangement and the needle, and this makes removal of the needle from the needle holder easier. In a preferred embodiment one connector is engaged by a lateral movement of the clip relative to the longitudinal axis of the needle and the other connector is engaged by a longitudinal movement relative to the longitudinal axis of the needle. The first connector may use a lateral movement, and the second connector may use a longitudinal movement. In this case, the needle is released from the guide arrangement by removing the clip from the guide arrangement. However, this leaves the clip connected to the needle. Therefore, in a preferred embodiment of the invention the first connector uses a longitudinal movement, and the second connector uses a lateral movement. Advantageously, this means that the clip may be removed from the guide arrangement by a movement of the clip along the length of the needle, and the clip can then be removed from the needle by a lateral movement. This means that neither the guide arrangement nor the needle are disturbed from their positions. Instead, the clip can be completely disengaged by movement of the clip alone.

The releasable connection may comprise any suitable mechanism. For example, a two part clip may be provided that can be fitted around a guide member of the guide arrangement and the needle by means of a screw thread, bayonet type fitting or the like. Preferably however, the releasable connection is achieved using a friction fit and/or resilient portions on the needle holder, such that the clip can be formed without moving parts, preferably as a single part, and can be connected to the needle and/or guide arrangement by pushing the clip toward the needle and/or guide arrangement respectively.

In a preferred embodiment the clip comprises a first connector and second connector as discussed above, wherein the first connector joins to a guide member of the guide arrangement by a tongue and groove arrangement. Advantageously, such a tongue and groove arrangement may allow the clip to slide along the guide member in order to place the needle at a desired angle and/or position. The tongue and groove arrangement may comprise a first channel on the clip for engagement with a tongue in the form of a rail portion of the guide member. The second connector may comprise a second channel for receiving the needle. Preferably, the first channel intersects the second channel, such that when the rail portion is inserted in the first channel, it prevents removal of the needle from the second channel. This arrangement allows the connection of the clip to the guide member to lock the needle in place, and hence avoids the need for an additional locking/closing piece to secure the needle. The first channel may, for example, extend normal to the second channel and pass across the second channel part way along the second channel so that the cross-sections of the two channels form a cross or T-shape when viewed along the longitudinal axis of the needle. With this arrangement, when the clip is in place, the rail portion bridges the second channel to block movement of the needle out of the second channel.

In order to ensure that the clip fits securely to the guide member, the first connector preferably includes a securing arrangement for providing a tightening connection as the clip is pushed onto the rail portion. This may be a resilient portion and/or an section of varying width on the clip and/or the rail portion. Preferably, the clip is arranged such that as the connection of the first channel with the rail portion is tightened, the needle is also more tightly engaged with the second channel. This may be achieved by clamping the needle between the rail portion and the base of the second channel. The base of the second channel may be the same surface as a side of the first channel. The needle holder may include a ridge and slot arrangement to guide the clip along the guide member. For example there may be a ridge or slot on an internal surface of the first channel, and a complimentary slot or ridge on an external surface of the rail portion. Engagement of a ridge with a slot can be used for guidance of a sliding motion of the clip along the guide member. In addition, this engagement can be used to positively secure the clip in a desired position.

The clip preferably includes a releasing device for facilitating disengagement of the clip from the rail portion. The releasing device may comprise lever portions for opening a channel or groove of the second connector. The opening may be achieved by resilient deformation of the clip.

The clip may be connectable to the needle and guide arrangement in two orientations, for example by rotating the clip through 180°. This may enable the clip to engage with the needle and/or guide arrangement in two different ways. In a preferred arrangement of this type, the clip includes a third connector in addition to the first connector, which joins to the guide member of the guide arrangement by a tongue and groove arrangement in a way similar to the first connector, and which preferably comprises a third channel, wherein when the rail portion is inserted in the third channel, it prevents removal of the needle from the second channel. The first connector may comprise a ridge or slot for engagement with a corresponding ridge or slot on the rail portion, in order to provide a guided sliding motion of the clip along the rail portion and/or to lock the clip in place. A second ridge or slot on the rail portion or the clip may provide a tighter coupling between the clip and guide member. In a particularly preferred embodiment, a ridge of the first connector engages with a first slot when pushed a first distance over the rail portion, which provides a guided sliding connection, and engages with a second slot when pushed further onto the rail portion, which fixes the clip in place. Preferably, the channel of the first connector intersects with the channel of the second connector such that a recess is provided for the needle, and the needle can be moved even when the first connector is fixed in place on the rail portion. With this arrangement, the third connector is preferably arranged to provide a tightening connection which securely fixes the clip and needle relative to the guide member. For example, a wedge shaped element may be used, for providing a resilient and/or friction fit between the clip and guide member.

The first connector and third connector may be on opposite sides of the clip such that either the first connector or the third connector can be selected to join the clip and optionally the needle to the guide member. In this way, the user can select if they want the needle to be securely held or not, by turning the clip to use the first connector or the third connector to join to the guide member.

The preferred clip and guide arrangements enable the connection between the needle and guide arrangement to be achieved using only one moving part. This is important for use in a medical environment and for cleaning, as it reduces the risk of contaminants, bacteria and so on being found in the clip. Moreover, the design of the clip enables medically compatible materials to be used, such as appropriate medically compatible plastics, which can readily be sterilised.

Preferably, the connectors of the clip have a degree of tolerance, such that the clip can securely support a needle even if the needle is not at the centre of the needle holder and/or the clip can securely support a needle at a range of angles relative to the clip. For example, the second channel may be larger than the desired needle size so that the needle sits loosely in this channel until secured in place. This arrangement makes it easier to connect and reconnect the needle holder part-way through a procedure, and also provides additional flexibility in adjustment of the needle position and angle.

In a preferred embodiment, the needle holder includes a base for supporting the needle holder when placed on a body surface. The base may include an adhesive layer for joining the needle holder to the body. The base should include a hole to allow passage of the needle from the guide arrangement to the body surface. Preferably, the hole has an opening in its perimeter, i.e. the base does not fully enclose the hole. This enables the user to fully remove needle holder from patient after the needle is disengaged from the guide arrangement, without the need to lift the needle holder base over the needle. Full engagement and disengagement of the needle holder can hence be achieved at any stage.

The base may include an arrow shaped portion, with the arrow preferably being directed toward the centre of the hole. The arrow shaped portion aids in centring the needle holder on the desired location on the body surface. Preferably, a plurality of arrow shaped portions are present, and these may be located symmetrically about the centre of the hole.

The guide arrangement may be any suitable mechanism for allowing the needle to be directed into the body at a range of angles. For example, guide arrangements similar to those in the above referenced prior art documents may be used, provided they can be adapted to work with the releasable clip of the present invention. In a preferred embodiment, the guide arrangement comprises a first guide member, and a second guide member. The first guide member corresponds to the guide member referred to above, and comprises a rail portion forming a segment of a circle. This first guide member may be supported by hinges on a base. The hinges allow the first guide member to be placed at any angle to the base, across an arc of about 180°. The second guide member is for enabling control of the angle of the first guide member.

The second guide member preferably takes the form of a segment of a circle located adjacent one end of the first guide member, wherein the guide arrangement includes a releasable clamp for joining the two guide members, and the releasable clamp is arranged to releasable secure the first guide member to the second guide member at any angle. The releasable clamp may comprises a screw fitting.

The needle holder can be used with any conventional interventional imaging method, for example with CT guidance or fluoroscopic guidance. For CT guided procedures the skin surface is marked and so the needle holder can be centred about the skin entry point by aligning the base with the markings. However, for other techniques, such as fluoroscopic guidance, this is not the case. With fluoroscopic guidance x-rays are used to visualize the needle axis and direct it towards a lesion. To ensure that the needle holder can be accurately aligned with the target area during the use of x-ray imaging or other imaging techniques where the skin is not marked the needle holder may include markers. The markers should be visible with the desired imaging method. For example, radio opaque markers may be used for x-ray imaging. The use of markers ensures that the needle holder can be visualised. The markers are preferably located on the arrow shaped portions of the base to allow alignment of the base with the target area and/or located on the clip to allow visualisation of the clip position and orientation.

As is known, some image guided procedures involve the use of multiple needles, each of which needs to be inserted into the body in a controlled way to target a particular site. An example of such a procedure is radio frequency (RF) ablation. A preferred embodiment of the needle holder includes a plurality of releasable clips, each for holding a needle on the guide arrangement. In this way, multiple needles can be located on a single guide arrangement and directed at different angles. Preferably, the guide arrangement includes a first guide member as discussed above and the circular arc of the segment of a circle that forms the rail of the first guide member is centred on a point beneath the base. With this arrangement, when two needles placed at different angles using two clips on the first guide member, the longitudinal axes of the two needles on the guide member will converge on a point below the skin.

Preferably, the needle holder is provided with multiple guide arrangements which are arranged for directing one or more needles at different angles. For example, there may be two first and second guide members of the type discussed above, with each first guide member being rotatable relative to the base. The arcs of rotation of the two first guide members may be centred along parallel lines spaced apart such that, when, in use, needles are guided from each of the two first guide members at an angle into the patient's body, the longitudinal axes of the two needles on the different guide members will converge on a point below the skin.

In a preferred embodiment, there are two first guide members, as above, centred on parallel lines that are spaced apart, and each of the circular arcs of the segment of a circle that form the rails of the two first guide member are centred on points at the same depth beneath the base. With this arrangement two or more needles held by clips on each of the two first guide members (e.g. at least four needles in total) can be directed into the patient's body in a symmetrical fashion.

Each clip of the multiple clips is releasable and the use of a lateral movement relative to the needle to disengage the clip enables all the clips and hence the needle holder to be disengaged from the plurality of needles without movement of the needles. Hence, multiple needles can be located, as desired, and then the needle holder can be removed to permit unimpeded access to the patient during the procedure.

It will be appreciated that different interventional procedures require different sizes of needle. The clip of the present invention may be made with sufficient tolerance to accommodate a range of needle sizes. In a preferred embodiment, a number of clips for fitment to different sizes of needle are provided in order to allow an increased range of needle size. Advantageously, the different sizes of clip may be used with the same guide arrangement, as the clips can be disengaged and replaced. Hence, the invention extends to a needle holder kit comprising a needle holder as set out above, with a clip for needles of first size, and at least one additional releasable clip, the additional clip being for needles of a second, different, size. There may also be one or more further additional clips, for needles of a third, different, size, a fourth, different, size and so on. Multiple clips of each size may be provided. This will enable use of the needle holder with multiple needles of each different size.

These and other features and improvements of the present application and the resultant patent will become apparent to one of ordinary skill in the art upon review of the following detailed description when taken in conjunction with the several drawings and the appended claims.

BRIEF DESCRIPTION OF THE DRAWINGS

A preferred embodiment of the invention will now be described by way of example only and with reference to the accompanying drawings in which.

DETAILED DESCRIPTION

Figure 1:
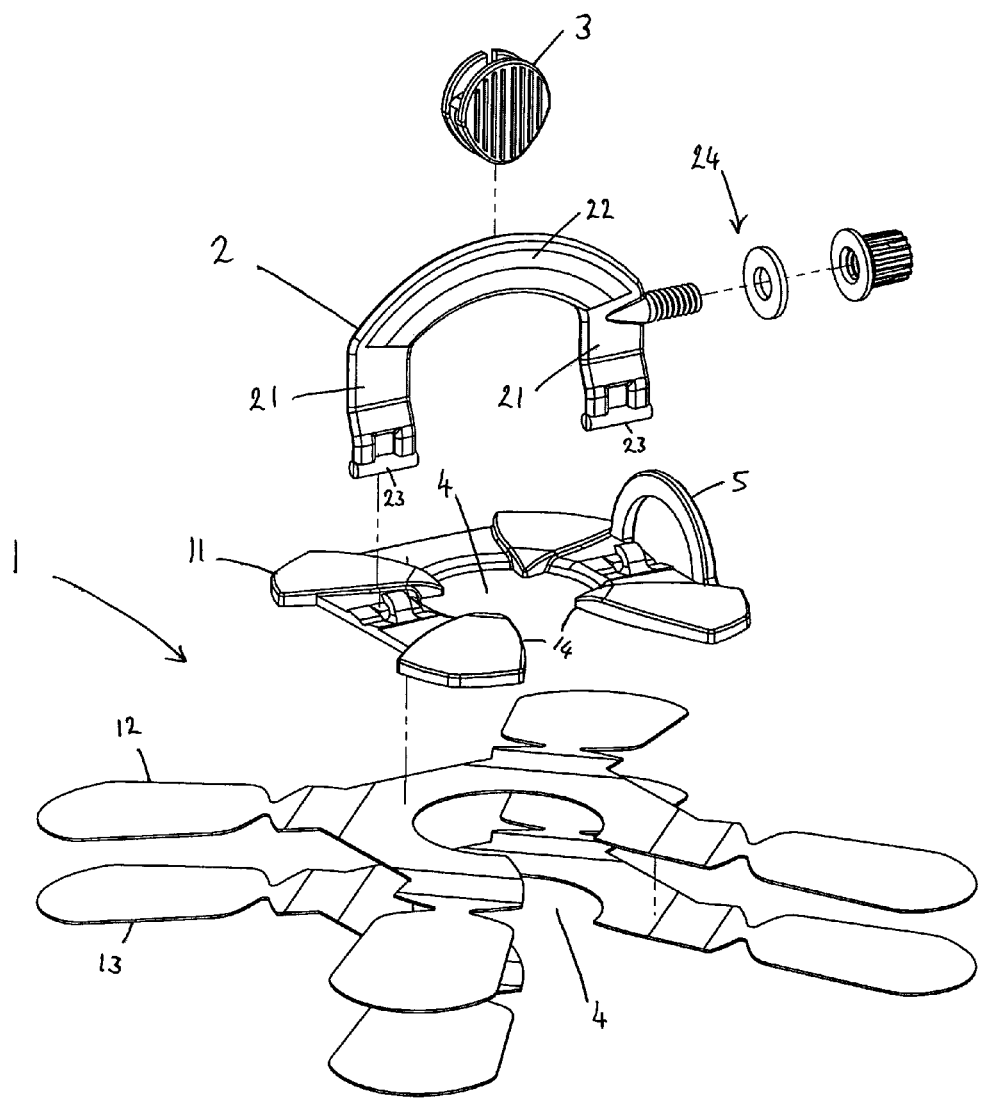
FIG. 1 is an exploded view of a needle holder, with a first embodiment of a clip.

As shown in FIG. 1, the needle holder is made up of a base 1, first guide member 2 and clip 3. The components of the base 1 each have a hole 4 at the centre, the hole 4 having an opening in its perimeter.

The base 1 comprises a rigid base plate 11, a flexible layer 12 and a tape layer 13, which is an adhesive tape. The flexible layer 12 and tape layer 13 have four arms extending outwardly from the central hole 4. These arms enable the base 1 to be adhered to the patient in a secure and flexible manner, if required, by means of the adhesive tape. The base plate 11 includes four arrow shaped portions 14, with the arrows being directed toward the centre of the hole 4. These arrow shaped portions 14 aid in centring the needle holder on the desired location on the body surface. Markers such as radio opaque markers can be placed on the arrow shaped portions 14 and also on the clip 3 to permit visualisation and alignment of the needle holder with a target area during an imaging procedure.

The first guide member 2 is an inverted U-shape, with two legs 21 supporting a rail portion 22, which is a segment of a circle. At the base of each of the legs 21 is a hinge member 23, for engagement with a bracket on the base plate 11. The hinge member 23 allows the first guide member 2 to pivot relative to the base 1. The base plate 11 incorporates a second guide member 5, which in this embodiment is formed integrally with the base plate 11. The second guide member 5 is a half circle, which is located adjacent one leg 21 of the first guide member 2 when the first guide member 2 is fixed to the base 1.

To enable controlled adjustment of the angle of the first guide member 2, the first guide member 2 includes a clamp mechanism 24. The clamp mechanism 24 comprises a screw thread integrally formed with the first guide member 2, and a washer and nut for attaching to the screw thread. The clamp mechanism 24 is tightened by screwing the nut onto the thread, and pressing the washer up against the second guide mechanism 5, to clamp it between the washer and the leg 21 of the first guide member 2. This can be seen more clearly in FIGS. 2 to 5.

Figure 2:
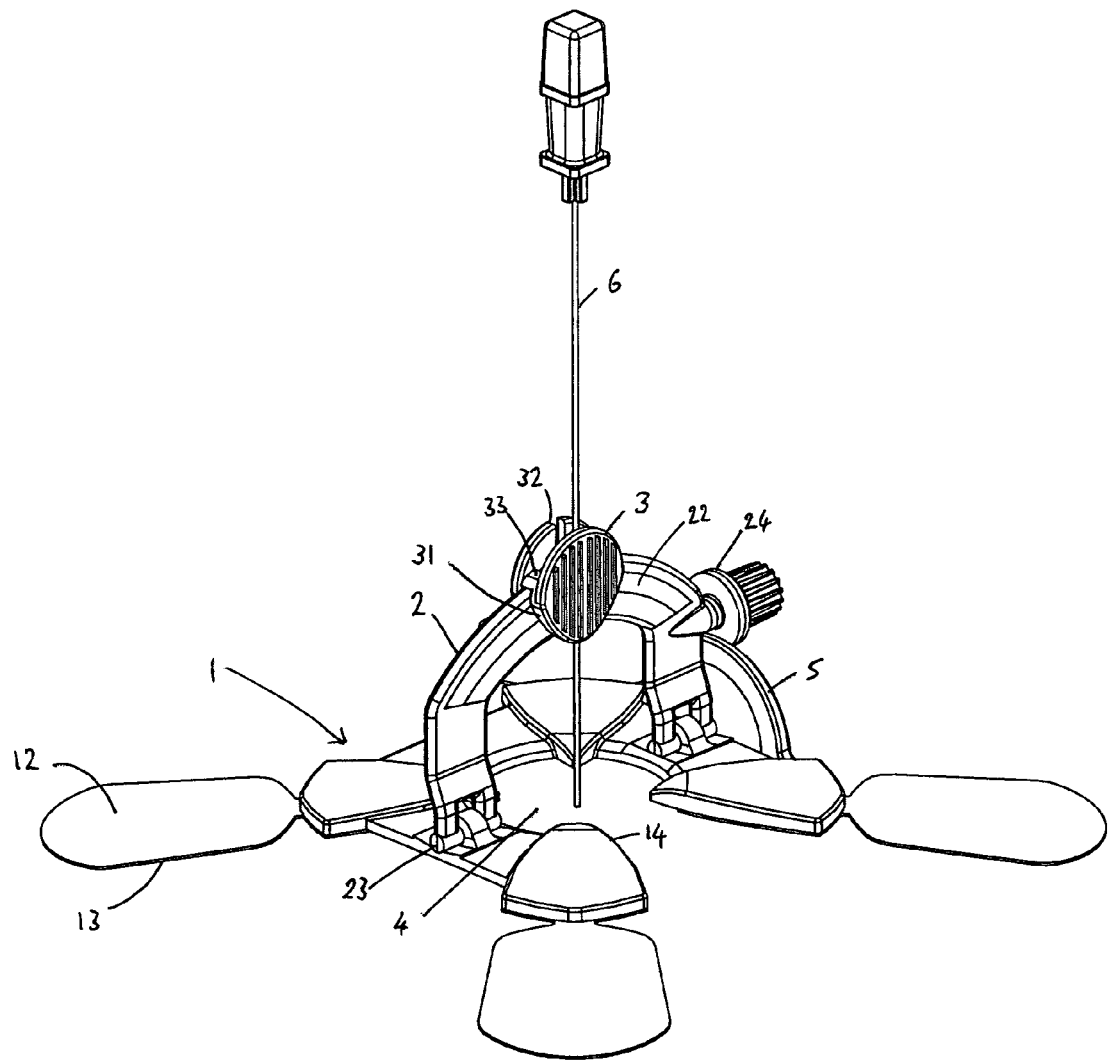
FIG. 2 is a perspective view of the needle holder of FIG. 1 with the needle present and being supported with its longitudinal axis normal to the base.

In FIG. 2 the needle holder of FIG. 1 is assembled and is in use supporting a needle 6, which is clamped between an internal surface of the clip 3 and the rail portion 22 of the first guide member 2. The hinges 23 are secured in the brackets on the base 1, and allow rotation of the first guide mechanism 2 relative to the base 1. The clamp mechanism 24 is engaged with the second guide mechanism 5 in order to secure the first guide mechanism 2 at an angle of about 90° to the base 1. The clip 3 is engaged with the first guide mechanism 2 such that the needle 6 is held vertically, i.e. normal to the body surface that the base 1 is supported by. The needle 6 can be inserted into the body through the hole 4.

It will be appreciated that the needle 6 can be supported at any desired angle by adjustment of the position of the clip 3 on the rail portion 22, and by adjustment of the angle of the first guide mechanism 2 to the base 1 using the second guide mechanism 5. The needle holder can thus be used to guide a needle into the body as discussed above.

Figure 3:
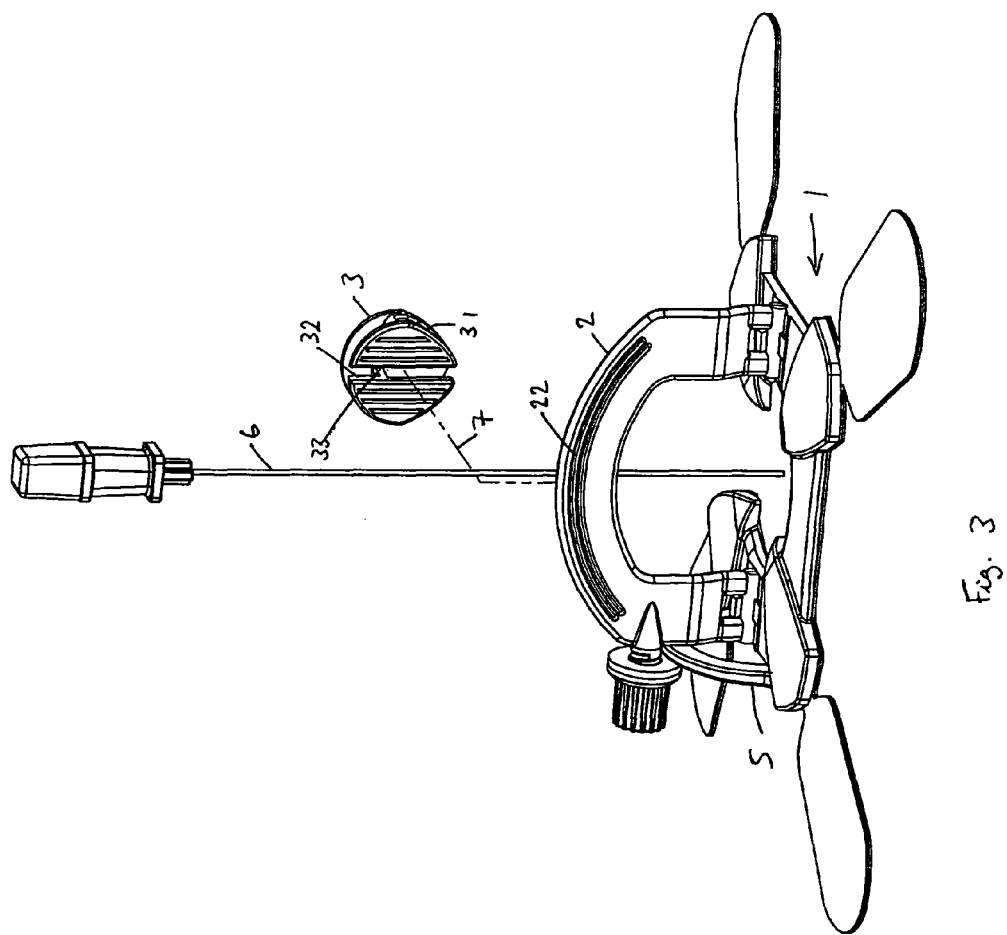
FIG. 3 shows the needle holder of FIG. 2 from the reverse side, with the clip removed from the first guide member and needle.
Figure 4:
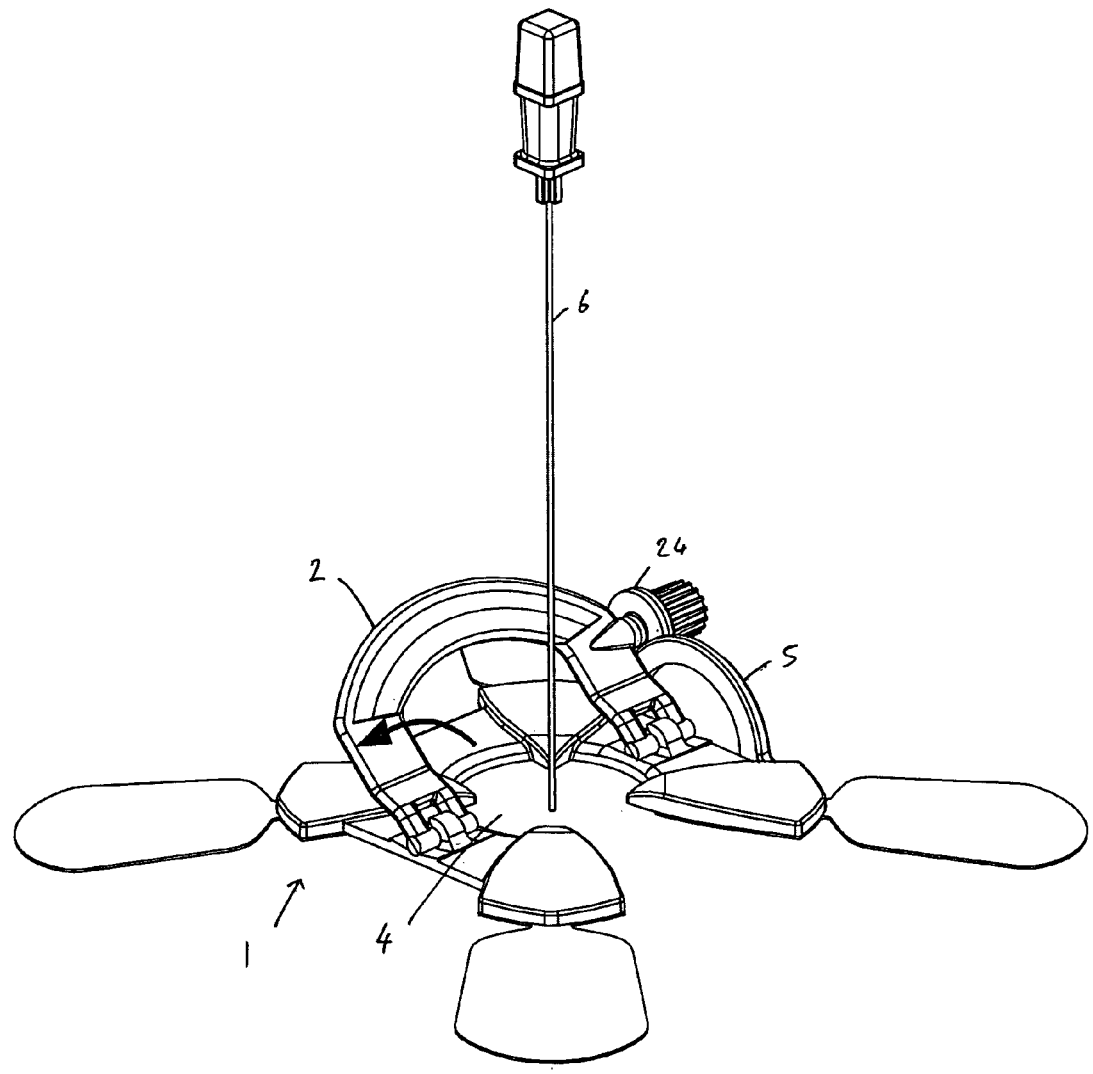
FIG. 4 illustrates rotation of the first guide member, in this case with the needle disengaged.

The clip 3 includes a first channel 31, which fits over the rail portion 22, and a second channel 32, which allows the needle 6 to be inserted in the clip 3. These parts of the clip 3 can be seen more clearly in FIG. 3, which shows the clip 3 disengaged from the first guide mechanism 2 and the needle 6. As shown in FIG. 3, the first channel 31 is formed between two outer flange portions of the clip 3, which extend in a generally vertical plane in the Figures. A central portion 33 joins the two outer flange portions, and extends in a generally horizontal plane in the Figures. Thus, in side view, i.e. viewed along the plane of the first guide mechanism 2 in FIG. 3, the clip 3 has a H-shape. The first channel 31 is formed by the lower half of the H-shape, between the two legs of the H. The second channel 32 is at right angles to the first channel 31, and cuts through one of the outer flange portions and through the central portion 33. The first channel 31 thus cuts through the second channel 32.

To secure the needle 6 to the needle holder, the clip 3 is moved sideways onto the needle 6 so that the needle 6 is placed in the second channel 32. Then, the clip 3 is slid along the length of the needle 6 so that the first channel 31 is pushed over the rail portion 22. These movements are shown by the dashed line 7 in FIG. 3. The rail portion 22 hence blocks movement of the needle 6 out of the second channel 32.

When the clip 3 is engaged with the rail portion 22, the needle 6 is clamped between the rail portion 22 and the internal surface of one of the outer flange portions of the clip 3. The clip 3 is arranged to fit tightly onto the rail portion 22 so that the needle 6 is securely held in place, and to this end the rail portion 22 includes ridges which engage with grooves on an internal surface of the clip 3. When the clip 3 is fully pushed onto the rail portion 22 there is a snap fit which locks the clip 3 in place. If the clip 3 is not fully pushed onto the rail portion 22 then it can slid along the ridges to enable adjustment of the needle angle. For a large adjustment of angle, the clip 3 can be fully removed, if required.

The clip 3 is composed of a resilient material, so it can be released from the rail portion 22 by pressing the two upper portions of the outer flanges together, which form lever portions for moving the two lower portions apart and widening the first channel 31. Thus, the clip 3 can be resiliently deformed by flexing the central portion 33.

Figure 5:
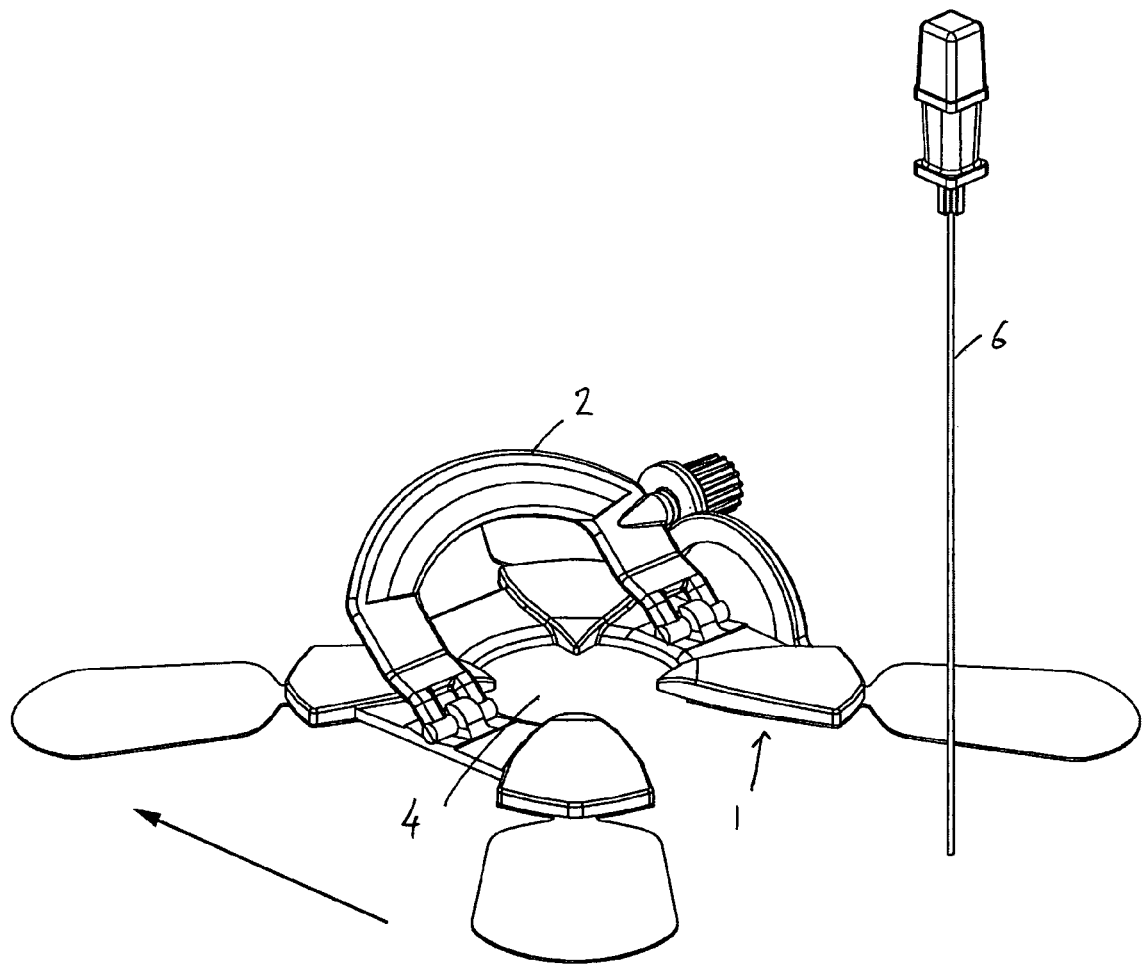
FIG. 5 shows the needle holder being withdrawn from the site of the procedure, with the needle remaining in place.

In FIG. 3, the clip 3 has been completely removed, and the first guide member 2 has been bent down away from the needle 6 as shown by the arrow. To do this, the clamp mechanism 24 can be loosened from the second guide member 5. This enables the needle 6 to be moved and/or fully inserted without hindrance. If required, the needle holder can be fully removed from the insertion area, by sliding the needle holder away from the needle 6 and passing the needle 6 through the opening of the hole 4, as shown in FIG. 5.

Figure 6:
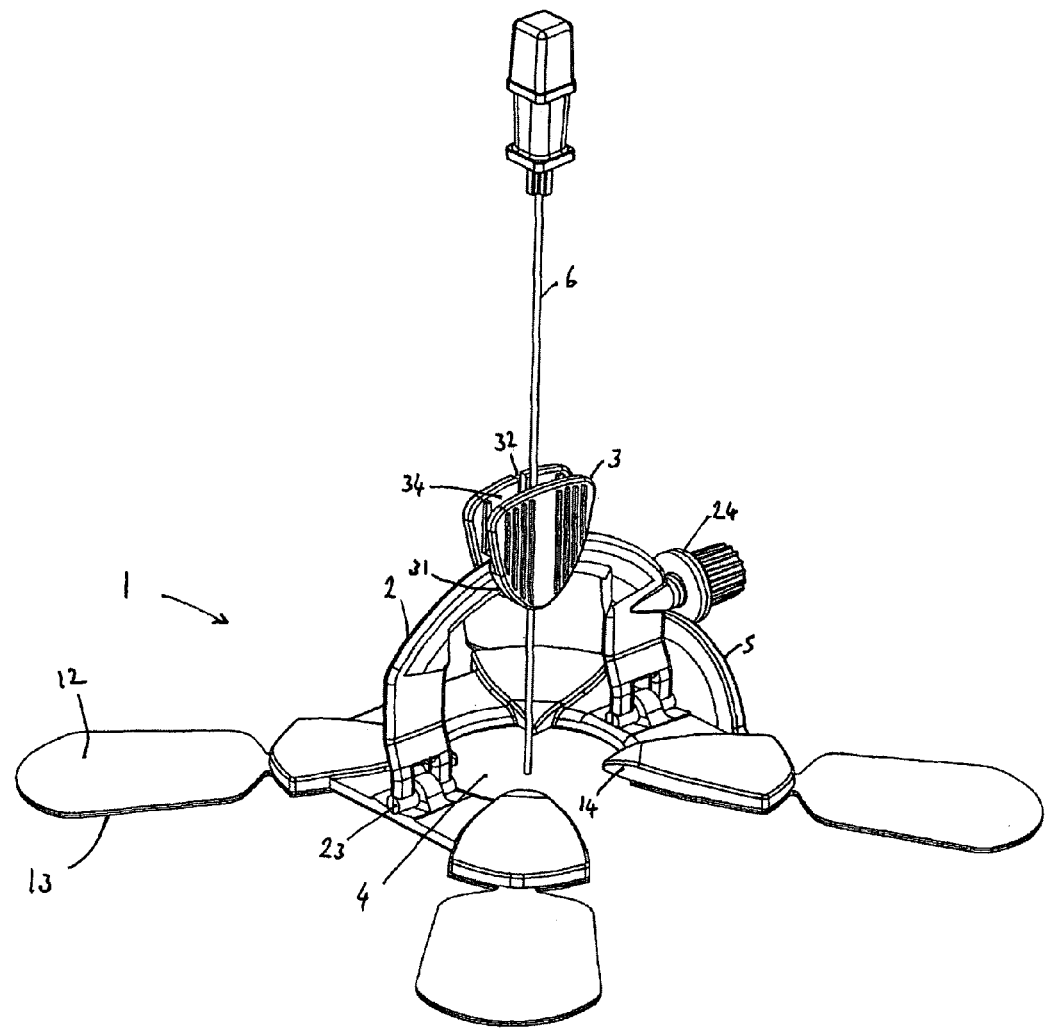
FIG. 6 illustrates a similar needle holder, with a second embodiment of a clip
Figure 7:
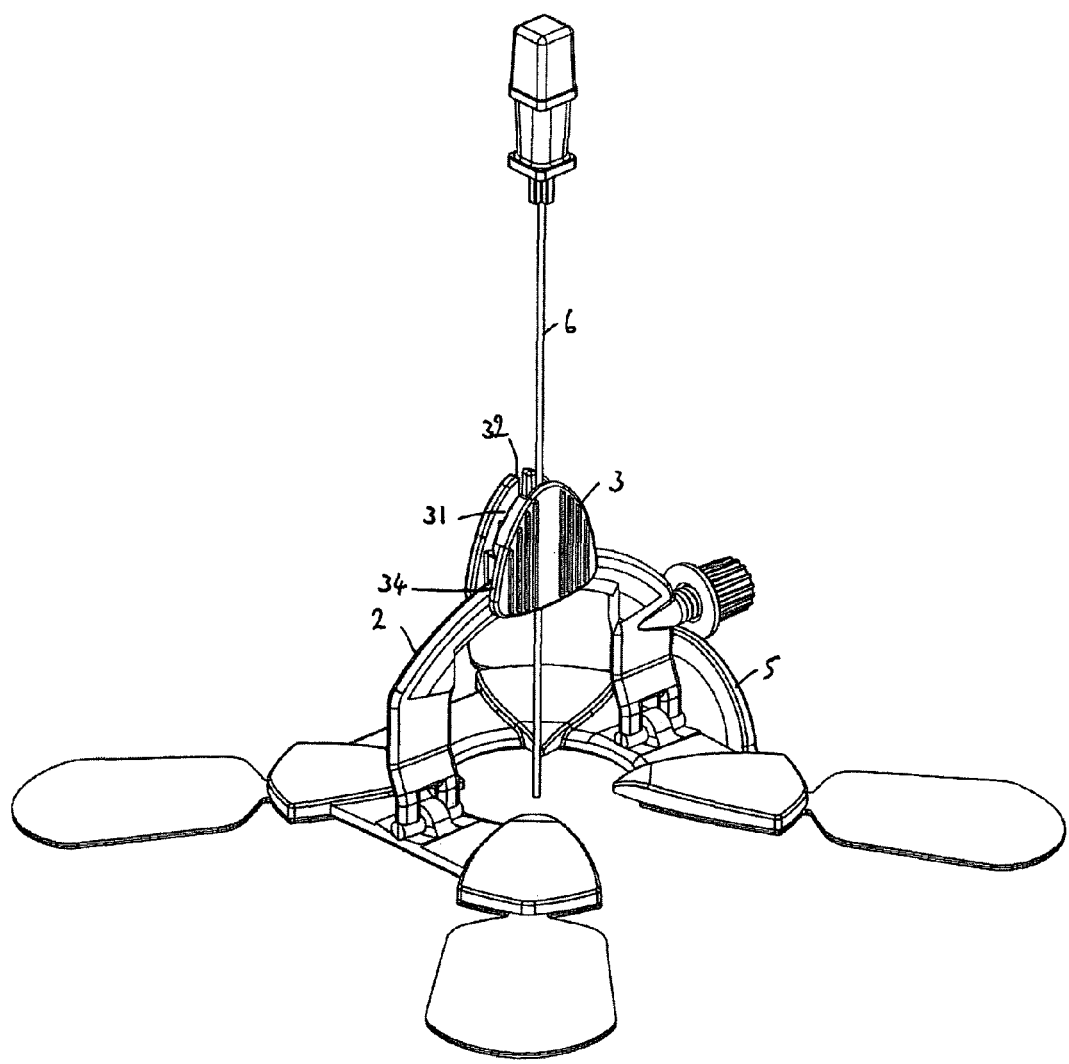
FIG. 7 shows the needle holder of FIG. 6, with the clip in a second orientation.

FIGS. 6 and 7 show a needle holder with a second embodiment of a clip 3. Other features of the needle holder in the second embodiment are the same as for FIGS. 1 to 5, as discussed above. The clip 3 is shown in a first orientation in FIG. 6, and in a second orientation in FIG. 7, where it is turned upside down compared to FIG. 6.

The clip 3 of the second embodiment includes a first channel 31, a second channel 32, two outer flange portions and a central portion 33 as in the first embodiment. The clip 3 of the second embodiment also makes use of a third channel 34. In the first orientation, the first channel 31 is engaged with the rail portion 22, and in the second orientation the third channel 34 is engaged with the rail portion 22. Engagement of the first or third channel is carried out by moving clip 3 sideways onto the needle 6 so that the needle 6 is placed in the second channel 32 and then sliding the clip 3 is slid along the length of the needle 6, as discussed above in relation to the first channel of the first embodiment.

Figure 8:
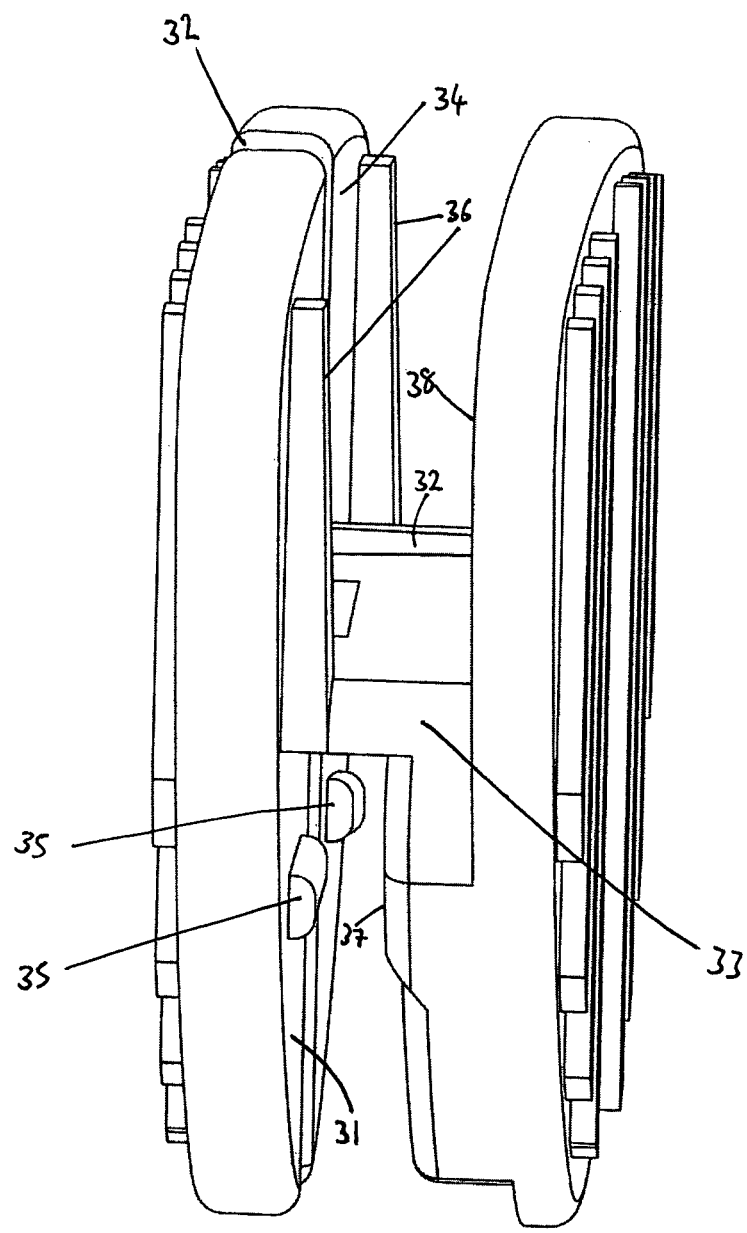
FIG. 8 shows the clip of FIG. 6 in greater detail.

The first channel 31 and third channel 34 of the clip 3 of the second embodiment can be seen in more detail in FIG. 8. The first channel 31 includes two ridges 35, and the third channel 34 includes two wedge shaped portions 36. These wedges 36 increase in width toward the middle of the clip 3. The second channel 32 intersects both the first and the third channels. The first channel 31 is narrower than the third channel 34, such that the second channel 32 extends beyond a side edge 37 of the first channel 31 to form a recess for the needle 6. The third channel 34 is wider, and a side edge 38 of the third channel 34 forms a continuous surface with the base of the second channel 32.

Figure 9:
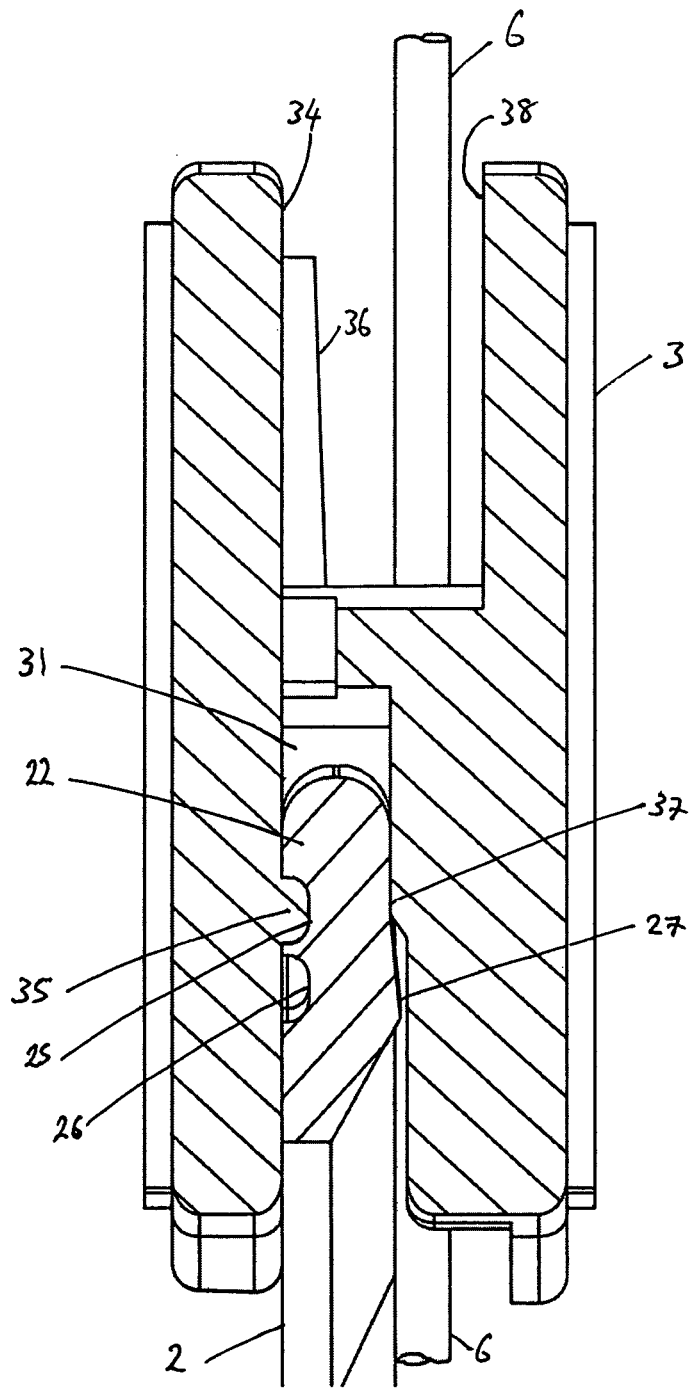
FIG. 9 is a cross-section with the clip of FIG. 6 in a first position.
Figure 10:
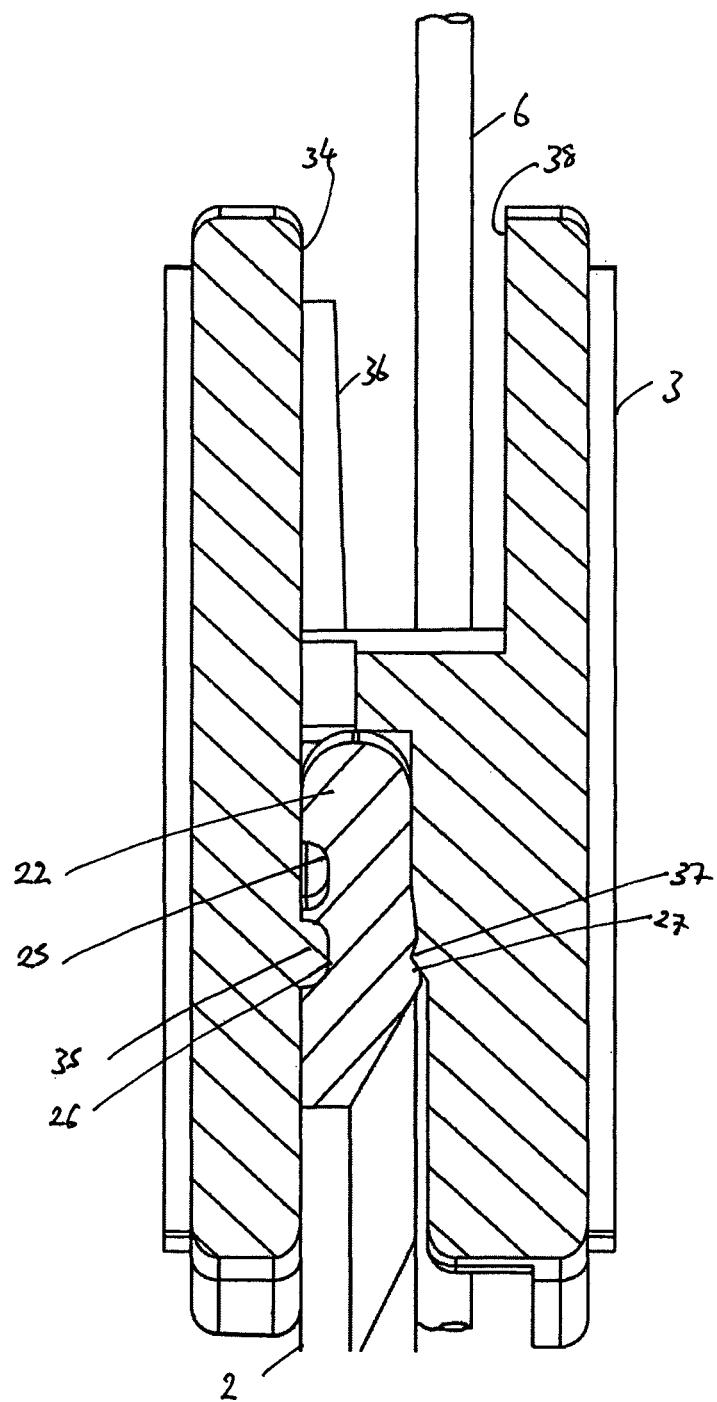
FIG. 10 is a similar cross-section showing the clip of FIG. 6 in a second position.
Figure 11:
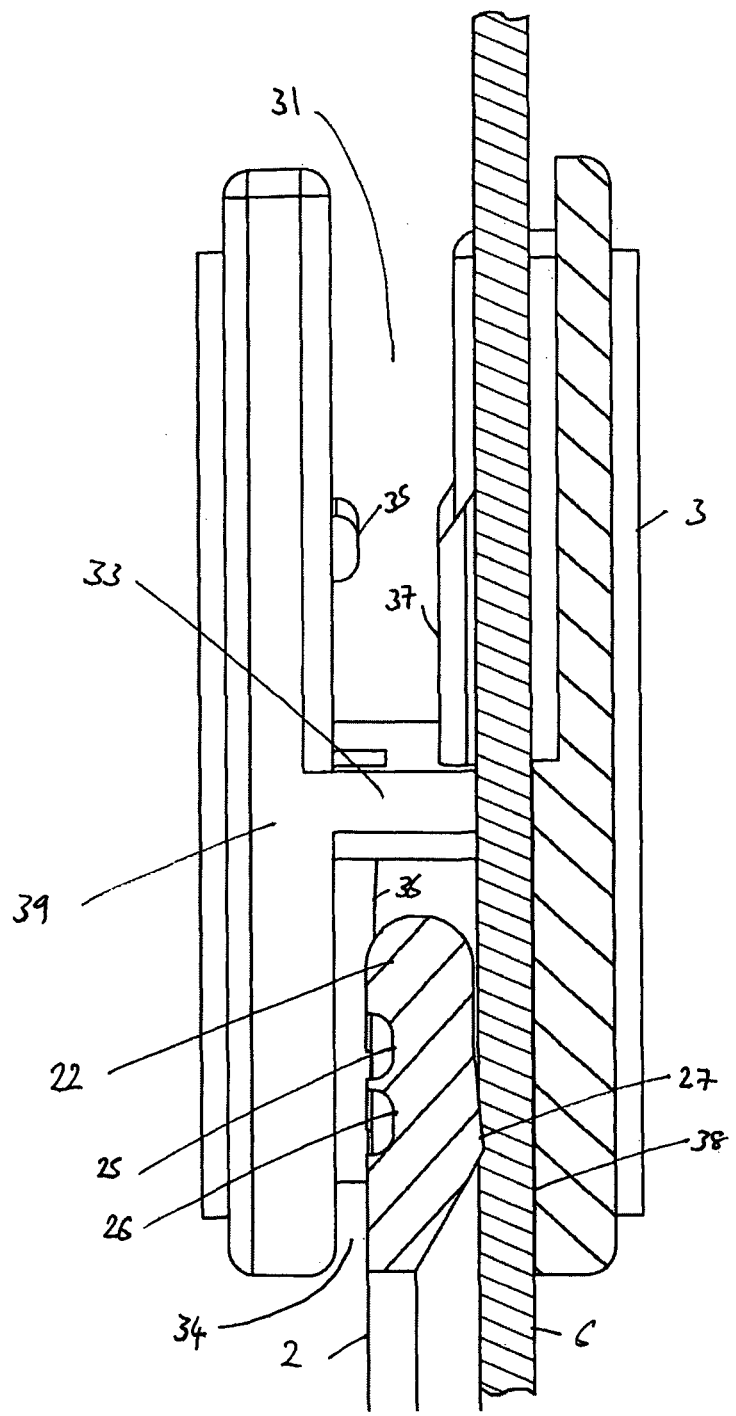
FIG. 11 shows a cross-section the clip in the second orientation, as in FIG. 7.

Operation of this clip 3 can be seen in FIGS. 9 to 11, which show detail of the clip 3 in cross-section for two positions in the first orientation, and also in the second orientation.

In FIG. 9 the clip is in the first orientation (as in FIG. 6), and hence the first channel 31 is engaged with the rail portion 22 of the guide member 2. The rail portion 22 includes two slots 25, 26 which are sized to fit the ridges 35 on the first channel 31 and are at a first and second height on the rail portion 22. In the first position of FIG. 9, the ridges 35 are engaged with the upper slot 25, and the first guide member 2 is hence held loosely within the first channel 31, such that the clip 3 can be slid to adjust the angle of the needle 6. If the clip 3 is pushed further onto the first guide member 2, the ridges jump in a snap fit from the upper slot 25 to the lower slot 26, as shown in FIG. 10. At the same time, an outwardly angled surface 27 of the first guide member 2, which is opposite the slots 25, 26, engages with the side edge 37 of the first channel opposite the ridges 35, and the clip 3 is locked in place by resilient deformation of the clip 3 and first guide member 2. With the clip 3 in the first orientation, the needle 6 cannot be removed from the second channel 32, but is free to move with the second channel 32 due to the recess formed beyond the side edge 37 of the channel. The needle 6 is shown placed against the angled surface 27 of the first guide member 2, and is free to move away from this surface 27 as far as the side edge 38 of the third channel 34, i.e. a movement to the right in the views shown in FIGS. 9 and 10.

FIG. 11 shows the clip 3 in its second orientation, upside down compared to FIGS. 9 and 11. The cross-section of FIG. 11 is translated into the page compared to the cross-sections of FIGS. 9 and 10, and cuts through the centre of the needle 6 and through the centre of the second channel 32. A wall 39 of the second channel can hence be seen. This Figure also illustrates how the second channel 32 cuts through the central portion 33 of the clip 3. In this orientation of the clip 3 the needle 6 can be securely fixed at a desired angle, by pushing the first guide member 2 between the wedges 36 and the needle 6. The rail portion 22 is pressed up against the wedges 36, and the outwardly sloped surface 27 is pressed up against the needle 6. This traps the needle 6 between the first guide member 2 and the side edge 38 of the third channel 34. Pushing the first guide member 2 further into the third channel 34 tightens the connection.

As for the first embodiment, the clip 3 is composed of a resilient material, so it can be released from the rail portion 22 by pressing the two upper portions of the outer flanges together, which form lever portions for moving the two lower portions apart and widening either the first channel 31 or the third channel 34, depending on the orientation of the clip 3.

The needle holder would typically be supplied sterilised and packed in a sterilised pouch for single use, and use of the needle holder might proceed as follows:

1. Clean, disinfect and cover the chosen entry point in a conventional manner.
2. Unpack the needle holder.
3. Centre the needle holder over the entry point using the four arrows 14 in the base plate 11 or markers located on the arrows 14. If a needle 6 is already in place locate the needle holder around it and centre the base 1 over the entry point.
4. Raise the first guide member 2 until it supports the needle 6 and fasten the screw of the clamping mechanism 24.

5. Chose the correct releasable clip 3 (for example, three or more sizes may be supplied for different needle thicknesses).

6. Attach the releasable clip 3 by movement along the dashed line 7 in FIG. 3, as discussed above.

7. If needed loosen the clamping mechanism 24 and/or the releasable clip 3 and adjust the positions of the first guide member 2 and clip 3 until the chosen needle angle is obtained. If the clip 3 of the second embodiment is used then this process will have the clip 3 in the first orientation.

8. Tighten the clamping mechanism 24 and push down the clip 3 to engage the snap fit, and thus secure the needle 6 at the chosen angulation. If the clip 3 of the second embodiment is used then this process will have the clip 3 in the second orientation.

9. Take a control image to verify the angulation. If not correct repeat steps 7-9.

10. If the control image confirms that the proper puncture route is obtained then loosen the clip 3 and insert the needle 6 further using the needle holder as stabilizer and guide.

11. Should there be a need to readjust the angulation loosen the clamping mechanism 24 and the clip 3 and align the needle 6 again.

12. Should there be a need for a large correction the clip 3 can be removed completely and the first guide member 2 pushed away.

13. If working with a coaxial system the needle holder can be used to secure an introducer needle in front of a lesion by changing the clip 3 to an undersized version. This means that the introducer needle is more firmly secured and will not be inadvertently pushed further in by manipulation of the inner needle. The clip 3 of the second embodiment is particularly suited to securing an undersized needle when in the second orientation. Alternatively a locking mechanism can be provided on the clip 3

14. The first guide member 2 can be reattached or removed depending on the need for support, and if required the needle holder can be completely removed as in FIG. 5.

If the interventional procedure requires multiple needles, then one or more additional clips and additional needles can be added by repeating steps as required.

The needle holder is made of different plastic materials, which are selected for their physical properties and to be compatible with various forms of sterilization among others ETO. Thus, the base plate 11 and guide members 2, 5 are polycarbonate, which is rigid and provides the required support. The clip 3 and the nut of the clamping mechanism 24 are polyurethane, which provides the required resilience. Both polycarbonate and polyurethane can be easily moulded into the desired shapes. The flexible layer 12 is made of a polyester.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

We claim:

1. A needle holder for use in an image guided intervention procedure comprising: a clip for holding a needle and a guide arrangement for supporting the clip and directing the needle at a desired angle relative to a patient's body; wherein the clip includes a releasable connection such that the needle can be disengaged from the guide arrangement by a lateral movement of at least one of the clip and the guide arrangement relative to the longitudinal axis of the needle; wherein the guide arrangement comprises a first guide member and a second guide member, the first guide member comprises a rail portion forming a segment of a circle, wherein the clip is supported on the first guide member and can be slid along the circular segment in order to direct the needle at the desired angle relative to the patient's body, and wherein the first guide member is joined to the clip and is supported by hinges on a base, wherein the second guide member is for controlling the angle of the first guide member relative to the base; and wherein the releasable connection comprises two parts of the clip fitted around the guide member by a screw thread or a bayonet fitting.

2. A needle holder as claimed in claim 1, wherein the clip includes a first connector for releasable engagement with the guide arrangement, and a second connector for releasable engagement with the needle.

3. A needle holder as claimed in claim 2, wherein one connector is arranged to be engaged with the guide arrangement by a lateral movement of the clip relative to the longitudinal axis of the needle and the other connector is arranged to be engaged with the guide arrangement by a longitudinal movement relative to the longitudinal axis of the needle.

4. A needle holder as claimed in claim 3, wherein the first connector uses a longitudinal movement and the second connector uses a lateral movement.

5. A needle holder as claimed in claim 2, wherein the first connector joins to a guide member of the guide arrangement by a tongue and groove arrangement that allows the clip to slide along the guide member in order to place the needle at a desired angle and/or position.

6. A needle holder as claimed in claim 5, wherein the tongue and groove arrangement comprises a first channel on the clip for engagement with a tongue in the form of a rail portion of the guide member.

7. A needle holder as claimed in claim 6, wherein the second connector comprises a second channel for receiving the needle, and the first channel intersects the second channel, such that when the rail portion is inserted in the first channel, it prevents removal of the needle from the second channel.

8. A needle holder as claimed in claim 2, wherein the first connector includes a securing arrangement for providing a tightening connection as the clip is pushed onto the rail portion.

9. A needle holder as claimed in claim 8, wherein the clip is arranged such that as the connection of the first channel with the rail portion is tightened, the needle is also more tightly engaged with the second channel.

10. A needle holder as claimed in claim 2, wherein the clip is connectable to the needle and guide arrangement in two orientations.

11. A needle holder as claimed in claim 10, wherein the clip includes a third connector, which joins to a guide member of the guide arrangement by a tongue and groove arrangement.

12. A needle holder as claimed in claim 11, wherein the third connector comprises a third channel on the clip for engagement with a tongue in the form of a rail portion of the guide member, and wherein when the rail portion is inserted in the third channel, it prevents removal of the needle from the second connector.

13. A needle holder as claimed in claim 12, wherein the third connector is arranged to provide a tightening connection which securely fixes the clip and needle relative to the guide member.

14. A needle holder as claimed in claim 2, wherein the first connector comprises a ridge or slot for engagement with a corresponding ridge or slot on a rail portion of the guide arrangement in order to provide a guided sliding motion of the clip along the rail portion.

15. A needle holder as claimed in claim 14, wherein a second ridge or slot on the rail portion or the clip is arranged to provide a tighter coupling between the clip and guide member.

16. A needle holder as claimed in claim 2, wherein, a channel of the first connector intersects with a channel of the second connector such that a recess is provided for the needle, and the needle can be moved even when the first connector is fixed in place on the guide arrangement.

17. A needle holder as claimed in claim 2, wherein the first connector comprises a ridge or slot for engagement with a corresponding ridge or slot on a rail portion of the guide arrangement in order to lock the clip in place.

18. A needle holder as claimed in claim 1, comprising a base for supporting the needle holder when placed on a body surface, wherein the base includes a hole to allow passage of the needle from the guide arrangement to the body surface.

19. A needle holder as claimed in claim 18, wherein the base has an opening into the hole at the perimeter of the hole.

20. A needle holder for use in an image guided intervention procedure comprising: a clip for holding a needle and a guide arrangement for supporting the clip and directing the needle at a desired angle relative to a patient's body; wherein the clip includes a releasable connection such that the needle can be disengaged from the guide arrangement by a lateral movement of at least one of the clip and the guide arrangement relative to the longitudinal axis of the needle; wherein the guide arrangement comprises a first guide member and a second guide member, the first guide member comprises a rail portion forming a segment of a circle, wherein the clip is supported on the first guide member and can be slid along the circular segment in order to direct the needle at the desired angle relative to the patient's body, and wherein the first guide member is joined to the clip and is supported by hinges on a base, and wherein the second guide member is for controlling the angle of the first guide member relative to the base.

21. A needle holder as claimed in claim 20, wherein the releasable connection comprises at least one of a connection between the clip and the guide arrangement and a connection between the clip and the needle.

22. A needle holder as claimed in claim 20, wherein the releasable connection is arranged to enable the needle to be disconnected from the clip by a lateral movement of the clip relative to the longitudinal axis of the needle.

* * * * *